April 27, 1965 H. C. BROWNELL Plant Pat. 2,499
ROSE PLANT
Filed Jan. 21, 1964
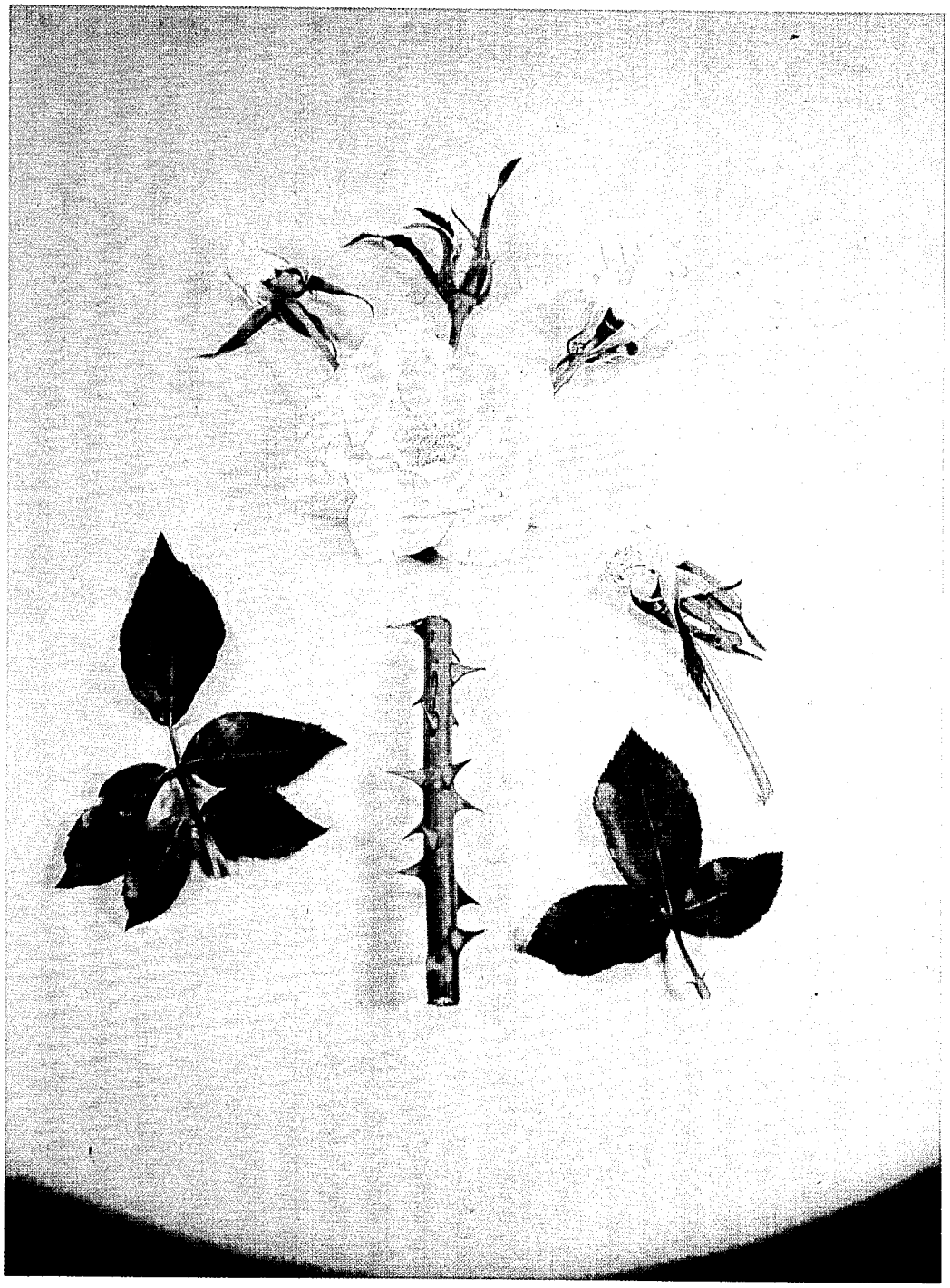
Inventor
Herbert C. Brownell United States Patent Office Plant Pat. 2,499
Patented Apr. 27, 1965

2,499
ROSE PLANT
Herbert C. Brownell, Little Compton, R.I.
Filed Jan. 21, 1964, Ser. No. 339,313
1 Claim. (Cl. Plt.—15)

My invention or discovery relates to roses and especially to a new, original and distinct variety of the class known commercially as "hybrid teas" and is a variant in that class, being a *Rosa wichuraiana* hybrid tea hybrid, produced by me and under my direction in the breeding grounds of my research gardens in Little Compton, Rhode Island, by selection of variety variations and by cross polination, which can be and has been asexually reproduced.

My new rose plant is new as to the following characteristics and especially as to their joint association with the characteristics inherited from *Rosa wichuraiana,* of hardiness, or immunity from serious injury on account of cold temperatures prevailing in certain parts of the Northern United States.

The deep orange to yellow color (ordinary dictionary definition) of its petals, in combination with the unique brilliance thereof and their tendency to hold these colors under extreme variable exposure;

The novelty and variation within certain definite limits of the form of the bloom, its character of holding its informal arrangement for a long time and the petallage of the flowers;

Its character of fragrance;

Its unusual abundance of flowers, notable after early bloom time and until frost;

The intensity of its remontant and everblooming or reblooming character;

The character of producing many seven leafleted leaves of exceptionally large size, the leaflets being frequently two inches in width and three inches in length, said leaves having a glossy varnish like appearance, which seven leafleted character seldom has obtained on hybrid teas not having *Rosa wichuraiana* ancestry, but frequently obtains on flower stems of descendants of *Rosa wichuraiana* of the dwarf reblooming type;

And especially its characteristic of partial freedom from premature defoliation by blackspot, under certain definite conditions of exposure, without any cultural control.

The following is a detailed description of my new variety, with color terminology in accordance with Robert F. Wilson's Horticulture Colour Chart, except for the stigma, which terminology is from Nickerson Color Fan of the American Horticultural Society.

*Essential information*

Type: Bush; outdoor; seedling; for cut flowers and for garden decoration.
Class: Hybrid tea.
Breeding: Seedling.
*Seed parent.*—"Helen Hayes," Plant Patent No. 1,509.
*Pollen parent.*—"Peace," Plant Patent No. 591.
Propagation: Holds its distinguishing characteristics through succeeding propagations by budding.

*Flower*

Locality where grown and observed: Little Compton, Rhode Island.

Flowers Borne: Singly and in clusters of three or five blooms.
Quantity of bloom: Very abundant outdoors.
Continuity: Nearly continuous from late June until frost.

Fragrance: Medium to strong.
Bud:
*Peduncle.* — Medium length; medium diameter; strong; erect; bark has hairy appendages.
*Color.*—Spinach Green o960.
*Before calyx breaks.*—The size is medium, form short pointed with calyx extending about ¾ of an inch beyond the tip of the bud.
*Color.*—Scheeles Green 860/1.
*As calyx breaks.*—Color (outside of petal) Orange 12/3 overlaid with Orange 12/2.
*Sepals.*—Long, narrow, pointed; with few foliaceous appendages along edges; permanent.
*Color.*—Outside Fern Green 0862. Inside Leak Green ooo58/3.
*As first petal opens.*—Color outside petal Yellow Ochre 07 overlaid with Persimmon Orange 710/1. Inside petal Spanish Orange 010.
*Opening.*—Opens up well outdoors in Little Compton, Rhode Island. Does not ball in excessive damp weather.
Bloom:
*Size (when fully open).*—Large; 4 inches to 5 inches.
*Petalage.*—Double; from 45 to 50 petals; arranged regularly.
*Form.*—Full and high centered at first, as flower opens petals recurl outward.
Petals:
*Texture.*—Thick; moderately leathery. Both inside and outside satiny.
*Shape.*—Orbiculate to cuneate; no notches.

This description of a newly opened flower was made from a rose grown out of doors in September at Little Compton, Rhode Island.

*Color.*—Outer petal: outside surface—Amber Yellow 505/3 with base of petal—Lemon Yellow 4/2; inside surface—Naples Yellow 403/1 with base of petal—Aureolin 3/1. Inner petal: outside surface—Chinese Yellow 606/2 with base of petal—Chinese Yellow 606; inside surface—Naples Yellow 403 with base of petal—Amber Yellow 505.

This description of a flower open for three days in September at Little Compton, Rhode Island.

Outside of petals top—Amber Yellow 505/2 shading to Chinese Yellow 606/2 near base of petal. Inside of petal—Maize Yellow 607/3 shading to Straw Yellow 604 near base of petal.

Reproductive organs:
*Stamens.*—Abundant, irregular in length.
*Filaments.*—Long; most with anthers. Color—Aureolin 3.
*Anthers.*—Medium large; color—Yellow Ochre 07.
*Pollen.*—Average; color—Amber Yellow 505.
*Pistils.*—Abundant; irregular in length.
*Stigma.*[1]—Color—Brillant Yellow 5Y9/9.
*Ovaries.*—Usually all enclosed in calyx.
*Hips.*—Short, round; color—Agathia Green 60.
*Seeds.*—Average number; from 6 to 8 per hip; usually medium size.

*Plant*

Foliage: Compound of usually 5 to 7 leaflets; from normal quantity to abundant.
*Leaflets.*—Shape—mostly cordate; edges slightly serrated.
*Color.* — Mature: upper surface — Ivy Green ooo1060/1; under surface — Parsley Green oo962/2. Mature leaflets occasionally 3½ inches in length and 2 inches in width. New growth:

[1] Nickerson Color Fan, American Horticultural Society.

upper surface—Parsley Green oo962; faint overlay Indian Lake 826; under surface—Lettuce Green 861/1 with overlay of Indian Lake 826.

*Rachis (the supporting stem of the compound leaf).*—Long; upper side grooved; with few stipitate glands on edges. Under side—smooth; no prickles.

*Stipules.*—Long, about 1 inch in length; with points short to medium length turning out at an angle of less than 45°.

*Disease resistance.*—Excellent resistance to mildew and blackspot as compared with other varieties grown under comparable cultural conditions at Little Compton, Rhode Island.

Growth:

*Habit.*—Bush; upright; much branched.

*Growth.*—Vigorous.

*Canes.*—Medium to heavy caliper.

*Main stems.*—Color—Lettuce Green 861.

*Thorns.*—Several; triangular shaped pointing horizontal. Color—Strong Brown [1] 2.5YR 4/7.

*Branches.*—From Lettuce Green 861 on one side

[1] Nickerson Color Fan, American Horticultural Society.

to Oxblood Red oo823 on the other side exposed to sun; hairs none.

*Thorns.*—Several; medium length; hooked, slightly downward; color—Oxblood Red oo823.

*New shoots.*—Color—from Lettuce Green 861 on one side; Oxblood Red oo823/1 on side exposed to sun. Thorns several, hooked, slightly downward.

*Color.*—Oxblood Red oo823.

*Hairs.*—None.

I claim:

A new and distinct variety of rose plant of the hybrid tea class, substantially as herein shown and described, characterized particularly as to novelty by its vigorous habit of growth, abundant glossy foliage of exceptional size and beauty, its large full bloom with its orange to yellow tones, its resistance to mildew and blackspot, and its ability to withstand moderate sub-zero temperatures in combination with its hybrid tea character and its *Rosa wichuraiana* ancestry.

No references cited.

ABRAHAM G. STONE, *Primary Examiner.*